US012564441B2

(12) United States Patent
    Govari et al.

(10) Patent No.:    US 12,564,441 B2
(45) Date of Patent:        Mar. 3, 2026

(54) BASKET CATHETER HAVING INSULATED ABLATION ELECTRODES AND DIAGNOSTIC ELECTRODES

(71) Applicant: Biosense Webster (Israel) Ltd., Yokneam (IL)

(72) Inventors: Assaf Govari, Haifa (IL); Christopher Thomas Beeckler, Brea, CA (US); Andres Claudio Altmann, Haifa (IL); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 18/616,638

(22) Filed: Mar. 26, 2024

(65)            Prior Publication Data
    US 2024/0225726 A1       Jul. 11, 2024
            Related U.S. Application Data

(63) Continuation of application No. 17/028,913, filed on Sep. 22, 2020, now Pat. No. 11,950,841.

(51) Int. Cl.
    *A61B 18/14*          (2006.01)
    *A61B 34/20*          (2016.01)
                (Continued)

(52) U.S. Cl.
    CPC .......... *A61B 18/1492* (2013.01); *A61B 34/20* (2016.02); *A61B 2017/00526* (2013.01); (Continued)

(58) Field of Classification Search
    CPC ...... A61B 18/1492; A61B 2018/00077; A61B 2018/00083; A61B 2018/00107; (Continued)

(56)            References Cited

U.S. PATENT DOCUMENTS 4,699,147 A     10/1987   Chilson et al.
    4,940,064 A      7/1990   Desai
                (Continued)

FOREIGN PATENT DOCUMENTS

CN      111248993 A      6/2020
    CN      111248996 A      6/2020
                (Continued)

OTHER PUBLICATIONS

Extended European Search Report dated Mar. 1, 2022, from corresponding European Application No. 21197900.0.
                (Continued)

*Primary Examiner* — Khadijeh A Vahdat

(57)            ABSTRACT

A catheter configured to be used in a medical procedure includes a shaft and electrically conductive splines. The splines can include an insulated portion and a non-insulated portion configured to electrically ablate tissue. The catheter can include one or more electrodes coupled to insulated portion(s) of the splines and configured to sense electrical signals in the tissue. The splines can be coupled to an apex, forming an expandable distal-end assembly. The catheter can include a bump stop coupled to the apex and configured to maintain a minimal distance between the apex and the distal tip of the shaft. An ablation system can include the catheter, a generator, and a processor configured to control ablation energy from the generator to the splines such that ablation energy is applied to a first spline without applying ablation energy to a second spline.

20 Claims, 3 Drawing Sheets

(51) Int. Cl.
    *A61B 17/00*         (2006.01)
    *A61B 18/00*         (2006.01)

(52) U.S. Cl.
    CPC .............. *A61B 2017/00867* (2013.01); *A61B 2018/00077* (2013.01); *A61B 2018/00083* (2013.01); *A61B 2018/00267* (2013.01); *A61B 2018/00351* (2013.01); *A61B 2018/00577* (2013.01); *A61B 2018/00613* (2013.01); *A61B 2018/1467* (2013.01); *A61B 2034/2051* (2016.02)

(58) Field of Classification Search
    CPC .. A61B 2018/0016; A61B 2018/00196; A61B 2018/00267; A61B 2018/00351; A61B 2018/00357; A61B 2018/00577; A61B 2018/00613; A61B 2018/00839; A61B 2018/1467; A61B 2017/00526; A61B 2017/00867; A61B 5/287; A61B 5/6858
    See application file for complete search history.

(56) References Cited

U.S. PATENT DOCUMENTS

| | | | |
|---|---|---|---|
| 5,215,103 A | 6/1993 | Desai |
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,391,199 A | 2/1995 | Ben-Haim |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,885,278 A | 3/1999 | Fleischman |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,119,030 A | 9/2000 | Morency |
| 6,162,179 A | 12/2000 | Moore |
| 6,216,043 B1 | 4/2001 | Swanson et al. |
| 6,216,044 B1 | 4/2001 | Kordis |
| 6,239,724 B1 | 5/2001 | Doron et al. |
| 6,292,695 B1 | 9/2001 | Webster, Jr. et al. |
| 6,332,089 B1 | 12/2001 | Acker et al. |
| 6,421,556 B2 | 7/2002 | Swanson |
| 6,428,537 B1 | 8/2002 | Swanson et al. |
| 6,456,864 B1 | 9/2002 | Swanson et al. |
| 6,484,118 B1 | 11/2002 | Govari |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,618,612 B1 | 9/2003 | Acker et al. |
| 6,690,963 B2 | 2/2004 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |

(56)                References Cited

U.S. PATENT DOCUMENTS

| | | | |
|---|---|---|---|
| 10,130,420 B2 | 11/2018 | Basu et al. | |
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |
| 10,278,590 B2 | 5/2019 | Salvestro et al. | |
| D851,774 S | 6/2019 | Werneth et al. | |
| 10,314,505 B2 | 6/2019 | Williams et al. | |
| 10,314,507 B2 | 6/2019 | Govari et al. | |
| 10,314,648 B2 | 6/2019 | Ge et al. | |
| 10,314,649 B2 | 6/2019 | Bakos et al. | |
| 10,349,855 B2 | 7/2019 | Zeidan et al. | |
| 10,350,003 B2 | 7/2019 | Weinkam et al. | |
| 10,362,991 B2 | 7/2019 | Tran et al. | |
| 10,375,827 B2 | 8/2019 | Weinkam et al. | |
| 10,376,170 B2 | 8/2019 | Quinn et al. | |
| 10,376,221 B2 | 8/2019 | Iyun et al. | |
| 10,398,348 B2 | 9/2019 | Osadchy et al. | |
| 10,403,053 B2 | 9/2019 | Katz et al. | |
| 10,441,188 B2 | 10/2019 | Katz et al. | |
| 10,470,682 B2 | 11/2019 | Deno et al. | |
| 10,470,714 B2 | 11/2019 | Altmann et al. | |
| 10,482,198 B2 | 11/2019 | Auerbach et al. | |
| 10,492,857 B2 | 12/2019 | Guggenberger et al. | |
| 10,542,620 B2 | 1/2020 | Weinkam et al. | |
| 10,575,743 B2 | 3/2020 | Basu et al. | |
| 10,575,745 B2 | 3/2020 | Solis | |
| 10,582,871 B2 | 3/2020 | Williams et al. | |
| 10,582,894 B2 | 3/2020 | Ben Zrihem et al. | |
| 10,596,346 B2 | 3/2020 | Aeby et al. | |
| 10,602,947 B2 | 3/2020 | Govari et al. | |
| 10,617,867 B2 | 4/2020 | Viswanathan et al. | |
| 10,660,702 B2 | 5/2020 | Viswanathan et al. | |
| 10,667,753 B2 | 6/2020 | Werneth et al. | |
| 10,674,929 B2 | 6/2020 | Houben et al. | |
| 10,681,805 B2 | 6/2020 | Weinkam et al. | |
| 10,682,181 B2 | 6/2020 | Cohen et al. | |
| 10,687,892 B2 | 6/2020 | Long et al. | |
| 10,702,178 B2 | 7/2020 | Dahlen et al. | |
| 10,716,477 B2 | 7/2020 | Salvestro et al. | |
| 10,758,304 B2 | 9/2020 | Aujla | |
| 10,765,371 B2 | 9/2020 | Hayam et al. | |
| 10,772,566 B2 | 9/2020 | Aujila | |
| 10,799,281 B2 | 10/2020 | Goertzen et al. | |
| 10,842,558 B2 | 11/2020 | Harlev et al. | |
| 10,842,561 B2 | 11/2020 | Mswanathan et al. | |
| 10,863,914 B2 | 12/2020 | Govari et al. | |
| 10,881,376 B2 | 1/2021 | Shemesh et al. | |
| 10,898,139 B2 | 1/2021 | Guta et al. | |
| 10,905,329 B2 | 2/2021 | Bar-Tal et al. | |
| 10,912,484 B2 | 2/2021 | Ziv-Ari et al. | |
| 10,918,306 B2 | 2/2021 | Govari et al. | |
| 10,939,871 B2 | 3/2021 | Altmann et al. | |
| 10,952,795 B2 | 3/2021 | Cohen et al. | |
| 10,973,426 B2 | 4/2021 | Williams et al. | |
| 10,973,461 B2 | 4/2021 | Baram et al. | |
| 10,987,045 B2 | 4/2021 | Basu et al. | |
| 11,006,902 B1 | 5/2021 | Bonyak et al. | |
| 11,040,208 B1 | 6/2021 | Govari et al. | |
| 11,045,628 B2 | 6/2021 | Beeckler et al. | |
| 11,051,877 B2 | 7/2021 | Sliwa et al. | |
| 11,109,788 B2 | 9/2021 | Rottmann et al. | |
| 11,116,435 B2 | 9/2021 | Urman et al. | |
| 11,129,574 B2 | 9/2021 | Cohen et al. | |
| 11,160,482 B2 | 11/2021 | Solis | |
| 11,164,371 B2 | 11/2021 | Yellin et al. | |
| 2001/0056273 A1 | 12/2001 | Ewers | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2004/0210121 A1 | 10/2004 | Fuimaono et al. | |
| 2006/0009689 A1 | 1/2006 | Fuimaono et al. | |
| 2006/0009690 A1 | 1/2006 | Fuimaono et al. | |
| 2006/0100669 A1 | 5/2006 | Fuimaono et al. | |
| 2007/0093806 A1 | 4/2007 | Desai et al. | |
| 2007/0276212 A1 | 11/2007 | Fuimaono et al. | |
| 2008/0161802 A1 | 7/2008 | Swanson et al. | |
| 2008/0234564 A1 | 9/2008 | Beatty et al. | |
| 2009/0171274 A1* | 7/2009 | Harlev | A61B 5/6859 |
| | | | 604/95.04 |
| 2010/0076426 A1* | 3/2010 | de La Rama | A61B 5/0036 |
| | | | 606/41 |
| 2011/0118726 A1 | 5/2011 | De La Rama et al. | |
| 2011/0160574 A1 | 6/2011 | Harlev et al. | |
| 2011/0190625 A1 | 8/2011 | Harlev et al. | |
| 2011/0245756 A1 | 10/2011 | Arora et al. | |
| 2011/0301597 A1 | 12/2011 | McDaniel et al. | |
| 2013/0172872 A1 | 7/2013 | Subramaniam et al. | |
| 2013/0172883 A1 | 7/2013 | Lopes et al. | |
| 2013/0178850 A1 | 7/2013 | Lopes et al. | |
| 2013/0190587 A1 | 7/2013 | Lopes et al. | |
| 2013/0296852 A1 | 11/2013 | Madjarov et al. | |
| 2014/0025069 A1 | 1/2014 | Willard et al. | |
| 2014/0052118 A1 | 2/2014 | Laske et al. | |
| 2014/0180147 A1 | 6/2014 | Thakur et al. | |
| 2014/0180151 A1 | 6/2014 | Maskara et al. | |
| 2014/0180152 A1 | 6/2014 | Maskara et al. | |
| 2014/0238175 A1 | 8/2014 | Huszar et al. | |
| 2014/0257069 A1 | 9/2014 | Eliason et al. | |
| 2014/0276712 A1 | 9/2014 | Mallin et al. | |
| 2014/0309512 A1 | 10/2014 | Govari et al. | |
| 2015/0011991 A1 | 1/2015 | Buysman et al. | |
| 2015/0045863 A1 | 2/2015 | Litscher et al. | |
| 2015/0080693 A1 | 3/2015 | Solis | |
| 2015/0105770 A1 | 4/2015 | Amit | |
| 2015/0119878 A1 | 4/2015 | Heisel et al. | |
| 2015/0133919 A1 | 5/2015 | McDaniel et al. | |
| 2015/0182282 A1 | 7/2015 | Zemel et al. | |
| 2015/0208942 A1 | 7/2015 | Bar-Tal et al. | |
| 2015/0250424 A1 | 9/2015 | Govari et al. | |
| 2015/0270634 A1 | 9/2015 | Buesseler et al. | |
| 2015/0342532 A1 | 12/2015 | Basu et al. | |
| 2016/0081746 A1 | 3/2016 | Solis | |
| 2016/0113582 A1 | 4/2016 | Altmann et al. | |
| 2016/0113709 A1 | 4/2016 | Maor | |
| 2016/0183877 A1 | 6/2016 | Williams et al. | |
| 2016/0228023 A1 | 8/2016 | Govari | |
| 2016/0228062 A1 | 8/2016 | Altmann et al. | |
| 2016/0278853 A1 | 9/2016 | Ogle et al. | |
| 2016/0302858 A1 | 10/2016 | Bencini | |
| 2016/0338770 A1 | 11/2016 | Bar-Tal et al. | |
| 2017/0027638 A1 | 2/2017 | Solis | |
| 2017/0065227 A1 | 3/2017 | Marrs et al. | |
| 2017/0071543 A1 | 3/2017 | Basu et al. | |
| 2017/0071544 A1 | 3/2017 | Basu et al. | |
| 2017/0071665 A1 | 3/2017 | Solis | |
| 2017/0095173 A1 | 4/2017 | Bar-Tal et al. | |
| 2017/0100187 A1 | 4/2017 | Basu et al. | |
| 2017/0143227 A1 | 5/2017 | Marecki et al. | |
| 2017/0156790 A1 | 6/2017 | Aujla | |
| 2017/0172442 A1 | 6/2017 | Govari | |
| 2017/0185702 A1 | 6/2017 | Auerbach et al. | |
| 2017/0202515 A1 | 7/2017 | Zrihem et al. | |
| 2017/0221262 A1 | 8/2017 | Laughner et al. | |
| 2017/0224958 A1 | 8/2017 | Cummings et al. | |
| 2017/0265812 A1 | 9/2017 | Williams et al. | |
| 2017/0281031 A1 | 10/2017 | Houben et al. | |
| 2017/0281268 A1 | 10/2017 | Tran et al. | |
| 2017/0296125 A1 | 10/2017 | Altmann et al. | |
| 2017/0296251 A1 | 10/2017 | Wu et al. | |
| 2017/0347959 A1 | 12/2017 | Guta et al. | |
| 2017/0354338 A1 | 12/2017 | Levin et al. | |
| 2017/0354339 A1 | 12/2017 | Zeidan et al. | |
| 2017/0354364 A1 | 12/2017 | Bar-Tal et al. | |
| 2018/0008203 A1 | 1/2018 | Iyun et al. | |
| 2018/0028084 A1 | 2/2018 | Williams et al. | |
| 2018/0049803 A1 | 2/2018 | Solis | |
| 2018/0085064 A1 | 3/2018 | Auerbach et al. | |

(56)        References Cited

U.S. PATENT DOCUMENTS

| | | |
|---|---|---|
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168503 A1 | 6/2018 | Waldhauser et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| JP | 2017522923 A | 8/2017 |
| JP | 2019503773 A | 2/2019 |
| WO | 9421167 A1 | 9/1994 |
| WO | 9421169 A1 | 9/1994 |
| WO | 1996005768 A1 | 2/1996 |
| WO | 9625095 A1 | 8/1996 |
| WO | 9634560 A1 | 11/1996 |
| WO | 0182814 B1 | 5/2002 |
| WO | 2004087249 A2 | 10/2004 |

(56) References Cited

FOREIGN PATENT DOCUMENTS

| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014124231 A1 | 8/2014 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |
| WO | 2020206328 A1 | 10/2020 |

OTHER PUBLICATIONS

Extended European Search Report dated Mar. 9, 2022, from corresponding European Application No. 21197898.6.

Search Reported with English translation dated Feb. 26, 2025, from corresponding Japanese Application No. 2021152919.

Decision to Grant A Patent with English translation dated Mar. 5, 2025, from corresponding Japanese Application No. 2021152919.

Search Reported with English translation dated Feb. 26, 2025, from corresponding Japanese Application No. 2021152915.

Decision to Grant A Patent with English translation dated Mar. 5, 2025, from corresponding Japanese Application No. 2021152915.

* cited by examiner

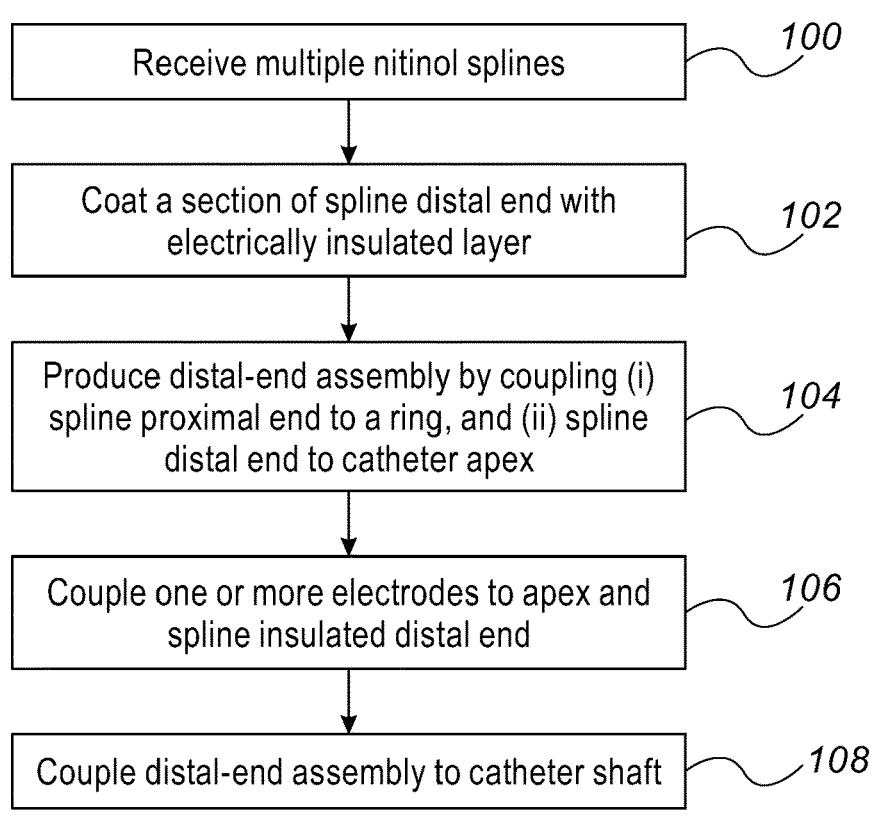

Receive multiple nitinol splines — 100

Coat a section of spline distal end with electrically insulated layer — 102

Produce distal-end assembly by coupling (i) spline proximal end to a ring, and (ii) spline distal end to catheter apex — 104

Couple one or more electrodes to apex and spline insulated distal end — 106

Couple distal-end assembly to catheter shaft — 108

*FIG. 4*

Insert into patient heart catheter having expandable distal-end comprising: (i) one or more splines having non-insulated section for tissue ablation and (ii) one or more sensing electrodes disposed on an insulated section of the splines and on apex — 200

Expand distal-end and couple apex to tissue for sensing intra-cardiac electrical signals — 202

Couple non-insulated section of splines to tissue and apply radiofrequency (RF) ablation pulses to tissue — 204

Collapse distal-end and extract catheter out of patient heart — 206

*FIG. 5*

BASKET CATHETER HAVING INSULATED ABLATION ELECTRODES AND DIAGNOSTIC ELECTRODES

CROSS-REFERENCE TO RELATED APPLICATIONS

This application is a continuation of prior filed U.S. patent application Ser. No. 17/028,913 filed on Sep. 22, 2020, now U.S. Pat. No. 11,950,841, which is related to U.S. patent application Ser. No. 17/028,907 filed on Sep. 22, 2020 and published as U.S. Patent Pub. No. 2022/0087734 on Mar. 24, 2022, now U.S. Pat. No. 11,950,840, each of whose disclosures are incorporated herein by reference.

FIELD OF THE INVENTION

The present invention relates generally to medical catheters, and particularly to ablation catheters having an expandable distal end.

BACKGROUND OF THE INVENTION

Basket catheters may be used in various medical applications, such as in cardiology. Several types of basket catheters, having multiple splines, are designed to enable sensing and treating of arrhythmia.

For example, U.S. patent Application Publication 2014/0238175 describes methods, systems, and devices for providing treatment to a target site. The system may include a guide assembly, an expandable support device coupled with the distal end of the guide assembly, and an operative member disposed on the expandable support device. The expandable support device may be configured to transition between a collapsed and expanded configuration.

U.S. Pat. No. 6,292,695 describes a method of controlling cardiac fibrillation, tachycardia, or cardiac arrhythmia by the use of an electrophysiology catheter having a tip section that contains at least one stimulating electrode, the electrode being stably placed at a selected intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

U.S. Pat. No. 6,421,556 describes systems and methods for diagnosing and treating tissue transmit an electrical energy pulse that temporarily stuns a zone of tissue, temporarily rendering it electrically unresponsive. The systems and methods sense an electrophysiological effect. due to the transmitted pulse. The systems and methods alter an electrophysiological property of tissue in or near the zone based, at least in part, upon the sensed electrophysiological effect. The alteration of the electrophysiological property can be accomplished, for example, by tissue ablation or by the administration of medication. In an implementation, radio frequency energy is used to both temporarily stun tissue and to ablate tissue through a common electrode.

U.S. patent Application Publication 2015/0182282 describes a variety of systems and techniques for generating and applying plasmas and/or electric fields alone, or in combination with other therapies, to living tissue to treat different tissue conditions as well as other conditions, such as tumors, bacterial infections and the like while limiting electrical current generation within said tissue. U.S. patent Application. Publication No. 2006/0100669 shows and describe a system for atrial fibrillation using a basket catheter.

SUMMARY OF THE INVENTION

An embodiment of the present invention that as described herein provides a catheter including a shaft for insertion into an organ of a patient, an expandable distal-end assembly, and one or more electrodes. The expandable distal-end assembly is coupled to the shaft and to an apex of the catheter, and includes multiple splines. In at least a given spline among the multiple splines, at least sixty (60) percent of a length of the given spline is non-insulated and is configured to make contact with tissue of the organ and to apply radiofrequency (RF) pulses to the tissue. The one or more electrodes are coupled to at least one of (i) an insulated section of one or more of the splines, and (ii) the apex, and, when placed in contact with the tissue, the one or more electrodes are configured to sense electrical signals in the tissue.

In some embodiments, the insulated section has at most forty (40) percent of the length of the given spline, and is positioned between the non-insulated length and the apex. In other embodiments, the insulated section is coated with an electrically-insulated layer. In yet other embodiments, at least the given spline includes nickel-titanium alloy.

In an embodiment, the apex has a flat surface, which is orthogonal to an axis of the shaft. In another embodiment, the catheter includes a processor, which is configured to produce an electrophysiological map of the tissue, indicative of the sensed electrical signals.

In some embodiments, first and second electrodes among the electrodes are disposed on the insulated section of the given spline, and the processor is configured to receive a bipolar signal sensed between the first and second electrodes. In other embodiments, the catheter includes third and fourth electrodes among the electrodes. The third electrode is disposed on an additional spline among the splines, and the fourth electrode is disposed on the apex. The processor is configured to receive at least one of: (i) a unipolar signal sensed between at least one of the electrodes and a reference electrode, and (ii) a bipolar signal sensed between any pair of the electrodes selected from among the first, second, third and fourth electrodes. In yet other embodiments, the catheter includes a bump stop, which is coupled to the apex and is configured to limit a minimal distance between the shaft and the apex.

There is additionally provided, in accordance with an embodiment of the present invention, a method for producing a catheter, the method includes receiving multiple splines. In at least a given spline among the multiple splines, at least sixty (60) percent of a length of the given spline is non-insulated for making contact with tissue of an organ of a patient and for applying radiofrequency (RF) pulses to the tissue, and at most forty (40) percent of the length of the given spline is insulated. The multiple splines are assembled together, such that the insulated length is positioned between the non-insulated length and an apex of the catheter for producing an expandable distal-end assembly. One or more electrodes are coupled to at least one of (i) the insulated length, and (ii) the apex, for sensing electrical signals when placed in contact with the tissue. The expandable distal-end assembly is coupled to a shaft of the catheter.

In some embodiments, the method includes coating the insulated length with an electrically-insulated layer.

There is further provided, in accordance with an embodiment of the present invention, a method including, inserting into an organ of a patient, a catheter having an expandable distal-end assembly that includes multiple splines, and in at least a given spline among the multiple splines, (i) at least sixty (60) percent of a length of the given spline is non-insulated for applying radiofrequency (RF) pulses to tissue of the organ, and (ii) at most forty (40) percent of the length of the given spline is insulated and is coupled to an apex of the catheter. At least one of the insulated length and the apex has one or more electrodes for sensing electrical signals in the tissue.

The present invention will be more fully understood from the following detailed description of the embodiments thereof, taken together with the drawings in which:

BRIEF DESCRIPTION OF THE DRAWINGS

FIG. 4 is a flow chart that schematically illustrates a method for producing a basket catheter having insulated ablation electrodes, in accordance with an embodiment of the present invention; and FIG. 5 is a flow chart that schematically illustrates a method for ablating tissue using the distal-end assembly of FIG. 3, in accordance with an embodiment of the present invention.

DETAILED DESCRIPTION OF EMBODIMENTS

Overview

Figure 1:
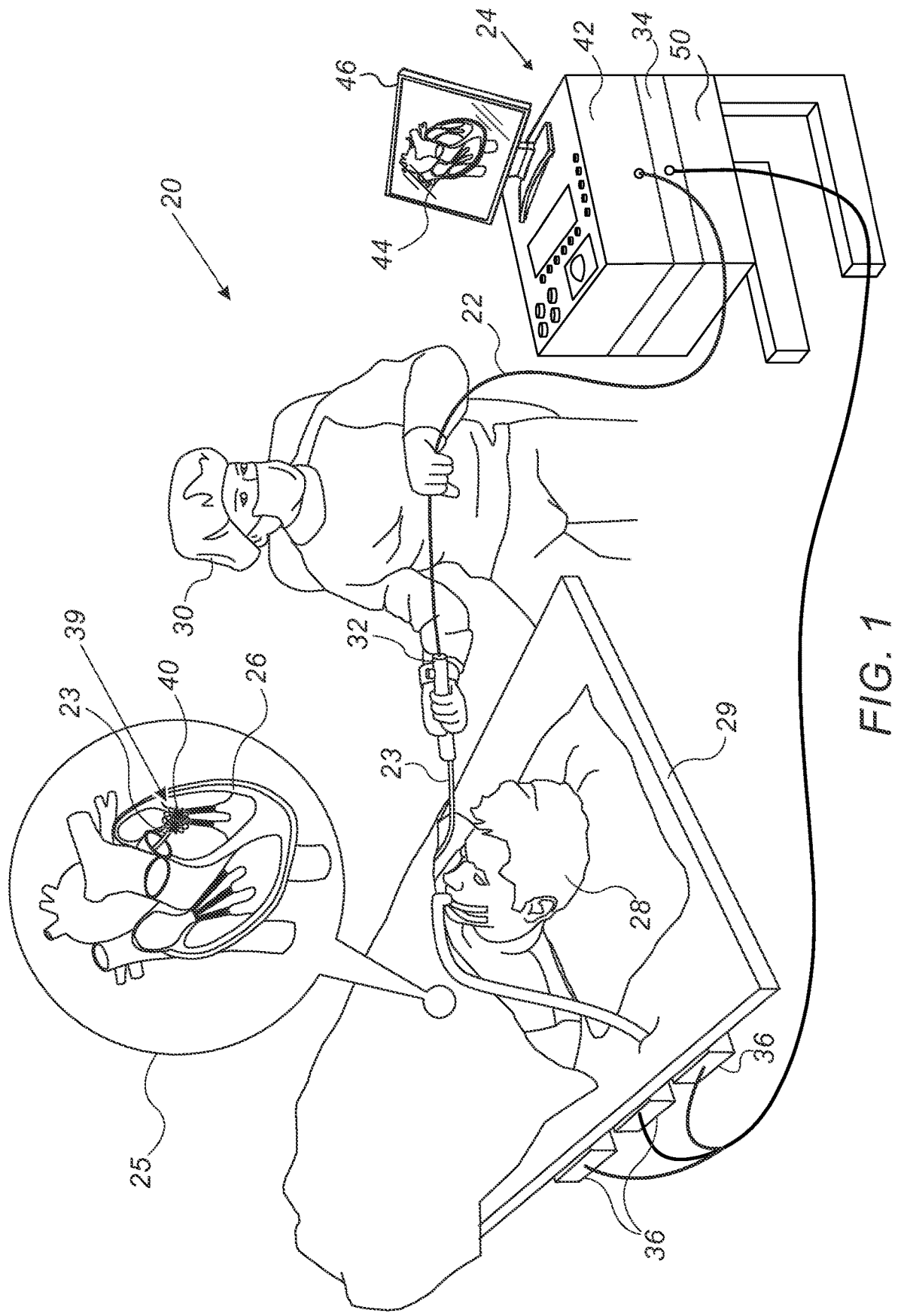
FIG. 1 is a schematic, pictorial illustration of a catheter-based position-tracking and ablation system, in accordance with an embodiment of the present invention.

Embodiments of the present invention that are described hereinbelow provide multiple configurations of improved distal-end assemblies used in a catheter of an ablation system. In some embodiments, the catheter comprises a shaft for inserting the distal-end assembly into a patient heart, and an expandable distal-end assembly, such as a basket, which is coupled to the shaft and to an apex of the catheter.

In some embodiments, the distal-end assembly comprises multiple splines, wherein at least one of, and typically all the splines are made from solid nitinol and have at least two sections. The first section of the splines is non-insulated, electrically conductive, and has at least sixty percent of the length of the splines. The first section is configured to make contact with tissue of the heart and to apply radiofrequency (RF) pulses to the tissue.

In some embodiments, the second section of the splines is insulated, comprises at most forty percent of the length of the splines, and positioned between the non-insulated section and the apex of the catheter. The insulated section may comprise the nitinol of the spline, which is coated with an electrically-insulated layer.

In some embodiments, the apex is electrically insulated from the spline and has a flat surface, which is orthogonal to an axis (e.g., longitudinal axis) of the shaft. Note that in the configuration described above, the first section is electrically conductive and is configured to ablate the heart tissue, whereas the second section and the apex are electrically insulated, and are configured to electrically insulate between the non-insulated sections of the splines. In such embodiments, in an ablation catheter having first and second splines, each of which having the first and second section, a processor of the ablation system is configured to control a radiofrequency (RF) pulse generator to apply one or more RF pulses to the first spline, without applying any RF pulses to the second spline.

Typically, prior to performing the ablation procedure, mapping of intra-cardiac signals is carried out, e.g., so as to define target tissue for ablation. In some embodiments, it is possible to use the non-insulated section of the splines for sensing the intra-cardiac signals. However, the non-insulated section, which comprises at least sixty percent of the spine, may have contact with a long section of the heart tissue, and therefore, may not be able to sense the intra-cardiac signals with sufficiently-high lateral resolution (e.g., about 1.0 mm) for mapping the tissue before ablation.

In some embodiments, the basket-shaped distal-end assembly described above, may comprise one or more diagnostic electrodes, also referred to herein as sensing electrodes. In the present example, the sensing electrodes are coupled to the electrically-insulated section and/or to the apex.

In some embodiments, one or more of the sensing electrodes are configured to sense unipolar signals, e.g., between the sensing electrode and a reference electrode attached to the skin or to any other tissue of the patient.

In other embodiments, two or more of the sensing electrodes are disposed on the apex and the insulated section and are configured to sense bipolar signals. For example, first and second sensing electrodes may be disposed on the insulated section of a first spline, a third sensing electrode may be disposed on the insulated section of a second spline, and a fourth sensing electrode may be disposed on the apex. In this configuration, the processor of the ablation system is configured to receive multiple bipolar signals from any pair from among the four sensing electrodes. For example, (i) a first bipolar signal between the first and second electrodes, (ii) a second bipolar signal between the second and third electrode, and (iii) a third bipolar signal between the third and fourth sensing electrodes.

The disclosed techniques are particularly effective for ablating (i) long and narrow tissue, e.g., when applying one or more RF pulses to a single spline, or (ii) long and wide tissue, e.g., when applying the RF pulses to multiple splines. Thus, the disclosed techniques may reduce the overall cycle time of an ablation procedure.

Moreover, the disclosed techniques reduce the need for attaching dedicated ablation electrodes to an expandable catheter, and therefore, improve the mechanical flexibility of the splines and reduce the costs associated with producing an expandable distal-end assembly of an ablation catheter.

System Description

FIG. 1 is a schematic, pictorial illustration of a catheter-based position-tracking and ablation system 20, in accordance with an embodiment of the present invention. in some embodiments, system 20 comprises a catheter 22, in the present example an expandable cardiac catheter, and a control console 24. In the embodiment described herein, catheter 22 may be used for any suitable therapeutic and/or diagnostic purposes, such as ablation of tissue in a heart 26 and for mapping cardiac arrhythmias by sensing intra-cardiac electrical signals.

In some embodiments, console 24 comprises a processor 42, typically a general-purpose computer, with suitable front end and interface circuits for receiving signals from catheter 22 and for controlling other components of system 20 described herein. Processor 42 may be programmed in software to carry out the functions that are used by the system, and is configured to store data for the software in a memory 50. The software may be downloaded to console 24 in electronic form, over a network, for example, or it may be provided on non-transitory tangible media, such as optical, magnetic or electronic memory media. Alternatively, some or all of the functions of processor may be carried out using an application-specific integrated circuit (ASIC) or any suitable type of programmable digital hardware components.

Reference is now made to an inset 25. In some embodiments, catheter 22 comprises a distal-end assembly 40 having multiple splines (shown in detail in FIGS. 2 and 3 below), and a shaft 23 for inserting distal-end assembly 40 to a target location for ablating tissue in heart 26. During an ablation procedure, physician 30 inserts catheter 22 through the vasculature system of a patient 28 lying on a table 29. Physician 30 moves distal-end assembly 40 to the target location in heart 26 using a manipulator 32 near a proximal end of catheter 22, which is connected to interface circuitry of processor 42.

In some embodiments, catheter 22 comprises a position sensor 39 of a position tracking system, which is coupled to the distal end of catheter 22, e.g., in close proximity to distal-end assembly 40. In the present example, position sensor 39 comprises a magnetic position sensor, but in other embodiments, any other suitable type of position sensor (e.g., other than magnetic-based) may be used.

Reference is now made back to the general view of FIG. 1. In some embodiments, during the navigation of distal-end assembly 40 in heart 26, processor 42 receives signals from magnetic position sensor 39 in response to magnetic fields from external field generators 36, for example, for the purpose of measuring the position of distal-end assembly 40 in heart 26. In some embodiments, console 24 comprises a driver circuit 34, configured to drive magnetic field generators 36. Magnetic field generators 36 are placed at known positions external to patient 28, e.g., below table 29.

In some embodiments, processor 42 is configured to display, e.g., on a display 46 of console 24, the tracked position of distal-end assembly 40 overlaid on an image 44 of heart 26.

The method of position sensing using external magnetic fields is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 1996005768, and in U.S. Patent Application Publications 2002/0065455 A1, 2003/0120150 A1 and 2004/0068178 A1, whose disclosures are all incorporated herein by reference.

Distal-End Assembly Having Insulated Ablation Electrodes

Figure 2:
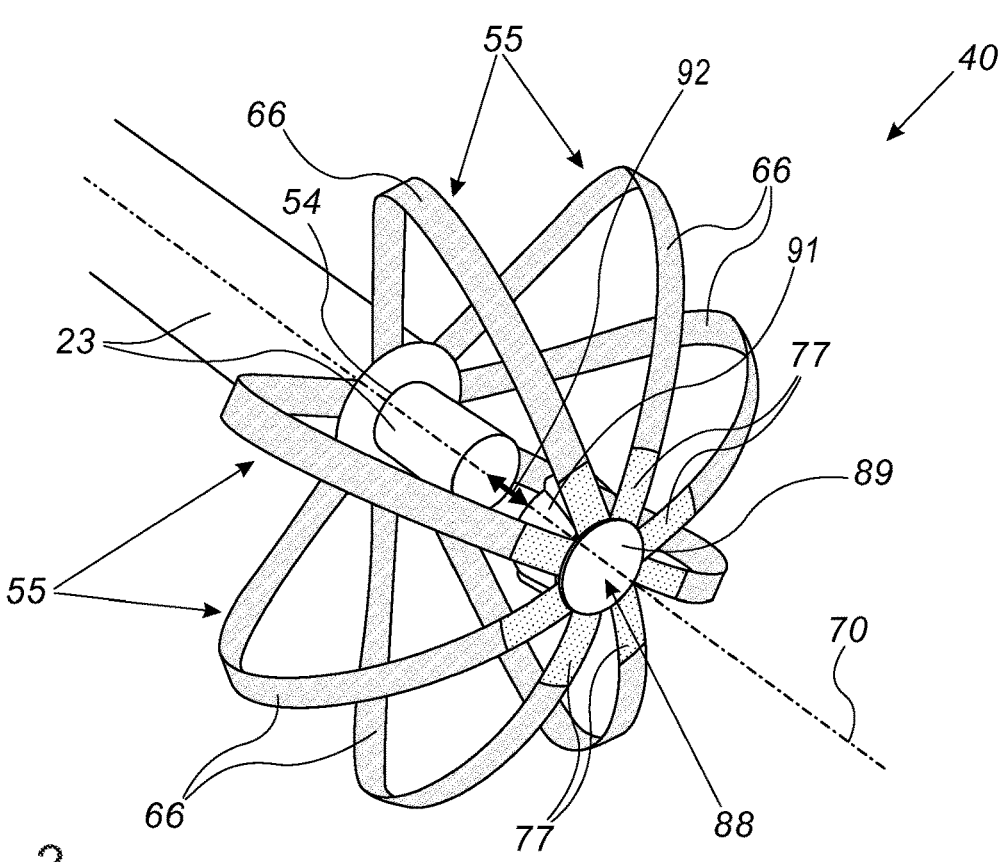
FIGS. 2 and 3 are schematic, pictorial illustrations of distal-end assemblies in an expanded position, in accordance with embodiments of the present invention.

FIG. 2 is a schematic, pictorial illustration of distal-end assembly 40 in expanded position, in accordance with an embodiment of the present invention.

In some embodiments, distal-end assembly 40 comprises multiple splines 55 made from solid nickel-titanium alloy, such as solid nitinol, or from any other suitable alloy or substance. Note that nitinol is selected for splines 55 for being electrically conductive and sufficiently flexible to conform to the tissue intended to be ablated. Thus, any other material selected for splines 55 has to be electrically conductive and sufficiently flexible to conform to the aforementioned tissue.

In some embodiments, at least a given spline 55, and typically each spline 55 of distal-end assembly 40, has an electrically-conductive section, referred to herein as a section 66, which is configured to serve as an ablation electrode for ablating tissue at the target location in heart 26.

In some embodiments, section 66 comprises at least sixty (60) percent of the length of spline 55. Section 66 is non-insulated (e.g., electrically conductive as described above) and is configured to make contact with tissue of heart 26, and to apply the radiofrequency (RF) pulses to the heart tissue during the ablation procedure.

In other embodiments, section 66 may comprise any other suitable portion of the length of spline 55.

In some embodiments, at least the aforementioned given spline 55, and typically each spline 55 of distal-end assembly 40, has a section 77, which is at most forty (40) percent of the length of the respective (e.g., given) spline 55. Section 77 is insulated and is positioned between section 66 and an apex 88 of catheter 22.

In some embodiments, section 77 is configured to electrically insulate between sections 66 of splines 55, at least at apex 88, which is typically electrically insulated from the spline. In other embodiments, apex 88 may comprise electrically conductive material(s) and may serve as an additional ablation electrode of distal-end assembly 40.

In some embodiments, apex 88 has a flat surface 89, which is typically (but not necessarily) orthogonal to an axis of shaft 23.

Note that section 66 has a typical length between about 10 mm and 40 mm. Therefore, when multiple splines 55 are applying pulses having predefined energy and duration, distal-end assembly 40 is configured to ablate an area of about 256 mm$^2$ in the tissue at the target location of heart 26.

In the context of the present disclosure and in the claims, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 71% to 99%.

In some embodiments, distal-end assembly 40 comprises a coupling element, in the present example a ring 54, which is coupled to the proximal end of splines 55 and is configured to be threaded on shaft 23 for coupling between shaft 23 and distal-end assembly 40. Note that each spline 55 is electrically connected to catheter 22, e.g., via wired (not shown) extended from the proximal end of each spline 55. Thus, processor 42 may control the electrical connectivity between console 24 and each section 66 of splines 55. This controlled and selective connectivity is important for applying the RF pulses via selected splines 55 to the tissue of heart 26, and similarly, to receive intra-cardiac electrical signal from selected electrodes placed in contact with tissue of heart 26 (e.g., sections 66 or other electrodes described in FIG. 3 below).

In some embodiments, when physician 30 moves the distal end of catheter 22 to the target location in heart 26, distal-end assembly 40 is in a collapsed position with all splines 55 straightened. When distal-end assembly 40 is positioned at the target location in heart 26, physician 30 typically reduces the distance between ring 54 and apex 88 (e.g., by pulling apex 88 toward ring 54, or by pushing ring 54 toward apex 88, or using any other technique), so as to have distal-end assembly 40 at an expanded position with splines 55 bent as shown in FIG. 2.

In some embodiments, distal-end assembly 40 comprises a bump stop 91, which is coupled to apex 88 and is configured to control a minimal distance between shaft 23 and apex 88. At the expanded position shown in the example of FIG. 2, distal-end assembly 40 may have a gap distance 92 (measured along the longitudinal axis 70) between the tip of shaft 23 and bump stop 91. The gap distance 92 can be any value from about 1 mm to 13 mm depending on the overall diameter of the catheter. In one preferred embodiment, the gap distance 92 is about 3 mm as measured along the longitudinal axis 70. In such embodiments, when physician 30 further reduces the distance between ring 54 and apex 88, bump stop 91 is configured to make contact with shaft 23, so that gap distance 92 does not exist (i.e., equals zero), and thereby to limit the minimal distance between shaft 23 and apex 88. In other words, bump stop 91 serves as a hard stop, which is configured to prevent the basket distal-end assembly 40 from going completely flat, and thereby, buckling the nitinol base.

In some embodiments, physician 30 may use manipulator 32 for controlling the distance between apex 88 and ring 54, and therefore the amount of expansion of distal-end assembly 40. Note that, when applying the RF pulses to distal-end assembly 40, section 66 serves as an ablation electrode and applies the RF pulses to the tissue in contact therewith, whereas section 77 is insulated, and therefore, does not apply the RF pulses to the tissue. Moreover, sections 77 are electrically isolating between sections 66 of distal-end assembly 40. In this configuration, processor 42 may control the RF pulse generator to apply one or more RF pulses to a first section 66 of a first spline 55 and not to apply any RF pulses to a second section 66 of a second spline 55.

Diagnostic Electrodes Coupled to the Apex of the Distal-End Assembly

Figure 3:
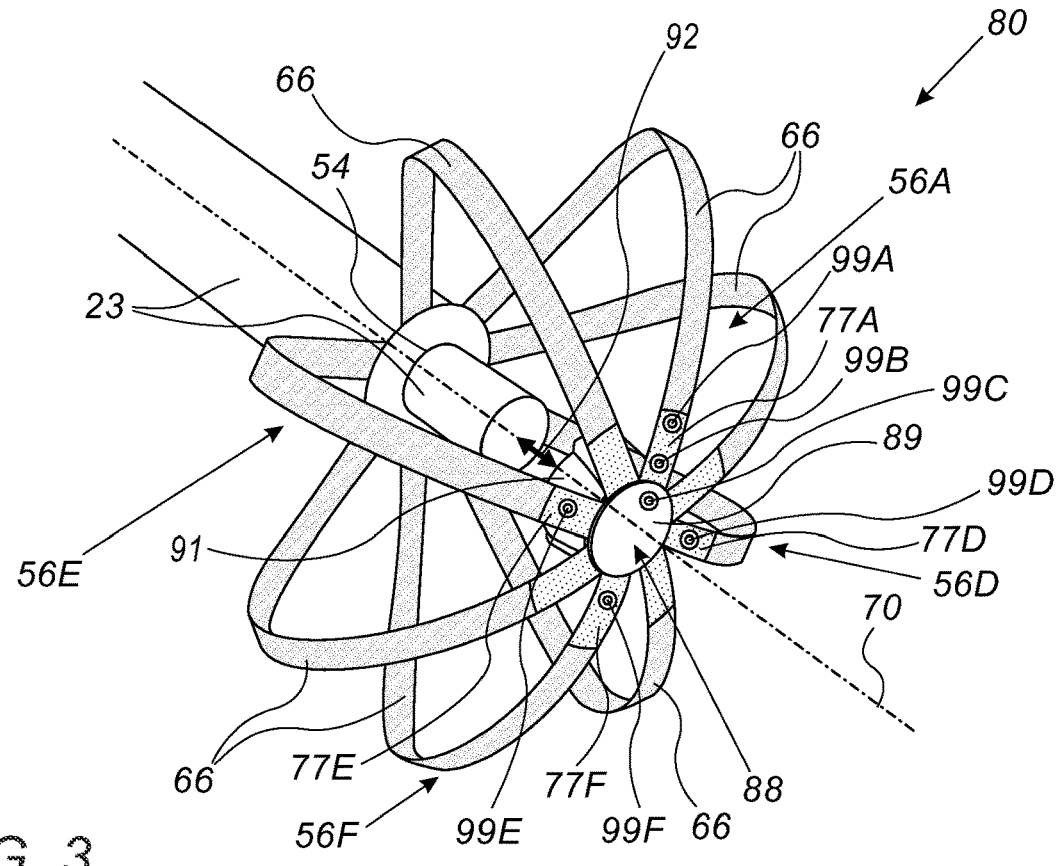

FIG. 3 is a schematic, pictorial illustration of a distal-end assembly 80 in expanded position, in accordance with another embodiment of the present invention. Distal-end assembly 80 may replace, for example, distal-end assembly 40 of FIG. 1.

In some embodiments, distal-end assembly 80 comprises multiple splines 56, such as splines 56A, 56D, 56E, and 56F similar to splines 55 of FIG. 2 above and having insulated sections 77A, 77D, 77E, and 77F, respectively. Each spline 56 of distal-end assembly 80 comprises non-insulated section 66 having the dimensions, mechanical and electrical attributes described in FIG. 2 above.

In some embodiments, distal-end assembly 80 comprises one or more diagnostic electrodes, referred to herein as electrodes 99. In the present example, electrodes 99 comprise (i) electrodes 99A and 99B, coupled to section 77A, (ii) electrode 99C, coupled to surface 89 of apex 88, (iii) electrode 99D, coupled to section 77D, (iv) electrode 99E, coupled to section 77E, and (v) electrode 998, coupled to section 77F. In other embodiments, distal-end assembly 80 may comprise and other suitable number of electrodes 99 disposed on any sections 77 and/or apex 88 using any suitable configuration.

In some embodiments, when placed in contact with the tissue of heart. 26, electrodes 99 are configured to sense electrical signals in the tissue. In the context of the present disclosure and in the claims, the terms "sensing," "mapping" and "diagnosing" are used interchangeably, wherein sensing electrodes (e.g., electrodes 99), which are configured for sensing the intra-cardiac signals, are producing signals used for mapping and diagnosing tissue in question of heart 26. In such embodiments, processor 42 is configured to produce, based on the intra-cardiac signals received from electrodes 99, an electrophysiological map of the tissue in question of heart 26.

In some embodiments, electrodes 99A and 99B are attached to section 77A of spline 56A, and are configured to sense a bipolar signal therebetween.

In some embodiments, a bipolar signal may be sensed between electrodes 99E and 99F, which are coupled to sections 77E and 77F of splines 56E and 56F, respectively. Additionally or alternatively, a bipolar signal may be sensed between electrode 99C that is coupled to surface 89, and electrode 99D that is coupled to section 77D of spline 56D. In other words, the bipolar signals may be sensed between (i) a pair of electrodes disposed on a single spline, and/or (ii) a pair of electrodes disposed on two different splines, and/or (iii) an electrode coupled to apex 88 and an electrode coupled to a spline, and/or (iv) a pair of electrodes (not shown) coupled to apex 88 at a predefined distance from one another, as shown for example on section 77A of spline 56A.

In other embodiments, at least one of electrodes 99 described above, is configured to sense a unipolar signal, for example relative to a reference electrode (not shown) placed in contact with tissue within the body of patient 28 or attached to the skin (not shown) of patient 28.

In some embodiments, electrodes 99 are coupled to respective sections 77 using any suitable technique, such as by crimping.

In some embodiments, distal-end assembly 80 may comprise electrical wires and/or electrical traces (neither shown), which are configured to electrically connect between each electrode 99 and processor 42. The electrical wires may be grouped in a braid running between console 24 and shaft 23, and at the distal end of shaft 23, each electrical wire is routed to a respective electrode 99.

In some embodiments, when distal-end assembly 80 is placed in contact with the tissue of heart 26, one or more of electrodes 99 are configured to generate potential gradient signals in response to sensed electrical potentials in the tissue of heart 26. Position sensor 39, which is fixed at the distal end of catheter 22 at a known distance from each electrode 99, is configured to generate position signals in response to the sensed external magnetic fields.

In some embodiments, based on (i) the position signal received from position sensor 39 and (ii) the signals received from one or more electrodes 99, processor 42 is configured to display, e.g., on display 46, an electrophysiological map of the electrical potentials sensed by electrodes 99 at respective locations in the tissue of heart 26.

In some embodiments, based on the electrophysiological mapping of the tissue of heart 26, physician 30 may position selected splines 56 in contact with the tissue to-be-ablated in heart 26. Subsequently, physician 30 and/or processor 42 may control system 20 to apply the RF pulses, so as to ablate the tissue of heart 26.

This particular configuration of system 20 and distal-end assemblies 40 and 80 are shown by way of example, in order to illustrate certain problems that are addressed by embodiments of the present invention and to demonstrate the application of these embodiments in enhancing the performance of such an ablation system. Embodiments of the present invention, however, are by no means limited to this specific sort of example system, and the principles described herein may similarly be applied to other sorts of medical systems, such as but not limited to electrosurgical systems and irreversible electroporation (IRE) ablation systems.

Producing Basket-Shaped Distal-End Assembly

FIG. 4 is a flow chart that schematically illustrates a method for producing distal-end assemblies 40 and 80, accordance with an embodiment of the present invention. The method begins at a spline receiving step 100, with receiving multiple splines 55 made from nitinol or from any suitable nickel-titanium alloy, or from any other alloy suitable to serve as an ablation electrode as described in FIGS. 2A and 2B above.

At a coating step 102, section. 77 of at least one of, and typically all splines 55 is coated with an electrically-insulated layer. At a distal-end assembly producing step 104, distal-end assemblies 40 and 80 are produced by coupling (i) the proximal end of all splines 55 to ring 54, and (ii) sections 77 located at the distal end of all splines 55 to catheter apex 88.

In other embodiments, one or more of splines 55 may already be coated with the aforementioned electrically-insulated layer at spline receiving step 100, so that step 102 may be redundant, and therefore, be excluded from the method.

At an electrodes coupling step 106, which is carried out only in the production of distal-end assembly 80, one or more electrodes 99 are coupled to apex 88 and/or to section 77 of one or more splines 55, and are connected to electrical wires for conducting signals between one or more (typically all) electrodes 99 and processor 42, as described in FIG. 2B above. Note that step 106 is not carried out in the production of distal-end assembly 40.

At a distal-end assembly coupling step 108, which concludes the method, distal-end assembly 40 or distal-end assembly 80 is coupled to shaft 23 along axis 70, as described in FIGS. 2A and 2B above. Note that in the production of distal-end assembly 40, after performing step 104, the method proceeds directly to step 108 without performing step 106, which is carried out only in the production of distal-end assembly 80.

In summary, steps 100, 102, 104 and 108 are used for producing distal-end assembly 40, and all steps 100, 102, 104, 106 and 108 are used for producing distal-end assembly 80.

This particular method of FIG. 4 for producing distal-end assemblies 40 and 80 is provided by way of example, in order to illustrate certain problems that are addressed by embodiments of the present invention and to demonstrate the application of these embodiments in producing distal-end assemblies 40 and 80 for enhancing the performance of system 20. Embodiments of the present invention, however, are by no means limited to this specific sort of example production processes, and the principles described herein may similarly be applied to other sorts of distal-end assemblies used in system 20 or in other sorts of medical systems, such as but not limited to electrosurgical systems and irreversible electroporation (IRE) ablation systems.

Performing Ablation Procedure Using the Basket-Shaped Distal-End Assembly

FIG. 5 is a flow chart that schematically illustrates a method for ablating tissue using distal-end assembly 80, in accordance with an embodiment of the present invention. The method begins at a catheter insertion step 200, with inserting distal-end assembly, which is described in detail in FIG. 3 below, into heart 26. In essence, one or more splines 56 of distal-end assembly 80 have: (i) section 66 configured for ablating the tissue of heart 26, and (ii) one or more electrodes, such as electrodes 99A-99F shown in FIG. 3 above, configured for sensing the intra-cardiac electrical signals in the tissue of heart 26.

At a sensing step 202, after placing distal-end assembly 80 in close proximity to tissue at the target location in heart 26, physician 30 controls the expansion of distal-end assembly 80 to the expanded position. The expansion may be carried out, for example, by reducing the distance between ring 54 and apex 88. Note that the minimal distance between ring 54 and apex 88 is limited by bump stop 91, as described in FIG. 1 above. In some embodiments, at sensing step 202, at least one of and typically both apex 88 and sections 77 (e.g., sections 77A, 77D, 77E and 77F) are coupled to the tissue for sensing the intra-cardiac electrical signals.

At an ablation step 204, based on the signals sensed in step 202, physician 30 manipulates distal-end assembly 80 and couples section 66 of one or more splines 56 (e.g., splines 56A, 56D, 56E and 56F) to the tissue for performing RF ablation. Note that in step 202 distal-end assembly 80 is positioned such that axis 70 is approximately orthogonal to the tissue for placing surface 89 of apex 88 in contact with the tissue for sensing. Moreover, in step 204, distal-end assembly 80 is positioned such that axis is approximately parallel to the tissue, so that one or more sections 66 are placed in contact with, and ablating the tissue.

At a catheter extraction step 206 that terminates the method, after concluding the ablation, physician 30 controls catheter 22 to collapse distal-end assembly 80 (e.g., by increasing the distance between ring 54 and apex 88), and subsequently, extracts catheter 22 out of the body of patient 28.

In other embodiments, processor 42 may hold the electrophysiological mapping of the tissue, before the ablation procedure or at least before step 202. In such embodiments, ablation step 204 is carried out based on the mapping after catheter insertion step 200, and sensing step 202 may be carried out after step 204, so as to check whether applying additional RF pulses is required after step 204 for concluding the ablation procedure. In case applying additional RF pulses is required, the method loops back to ablation step 204 followed by sensing step 202 for one or more iterations until concluding the ablation.

In alternative embodiments, sensing step 202 may be carried out before and after ablation step 204, so as to sense the intra-cardiac electrical signals for controlling the ablation process as described above.

Although the embodiments described herein manly address basket catheters, the techniques described herein can also be used in any other suitable medical probes having splines for applying energy to tissue.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. An ablation system comprising:
a catheter configured to be used in a medical procedure, the catheter comprising:
 a shaft extending along a longitudinal axis and comprising a distal tip;
 a plurality of electrically conductive splines coupled to the distal tip, each spline of the electrically conductive splines comprising an insulated portion and a non-insulated portion, the non-insulated portion being configured to make contact with a tissue of an anatomical structure and electrically ablate the tissue;
 an apex disposed at a distal end of the catheter, the plurality of electrically conductive splines being coupled to the apex and forming an expandable distal-end assembly between the distal tip of the shaft and the apex, wherein the apex comprises an insulated portion and an electrically conductive material disposed on the insulated portion, the electrically conductive material configured to make contact with tissue; and
 one or more electrodes coupled to the insulated portion of one or more splines of the plurality of electrically conductive splines, each of the one or more electrodes being configured to sense electrical signals in the tissue, and wherein the one or more electrodes are positioned to contact tissue simultaneously with the electrically conductive material of the apex;
a generator; and
a processor configured to:
 control ablation energy provided by the generator to the plurality of electrically conductive splines such that ablation energy is applied to a first spline of the plurality of electrically conductive splines without applying ablation energy to a second spline of the plurality of electrically conductive splines; and
 sense bipolar electrical signals in the tissue between an electrode of the one or more electrodes and the non-insulated portion of the apex.

2. The catheter of claim 1, wherein the electrically conductive material of the apex is further configured to deliver ablative energy to the tissue.

3. The catheter of claim 1,
wherein an electrode of the one or more electrodes is defined by the electrically conductive material and coupled to the insulated portion of the apex.

4. The catheter of claim 1, further comprising:
a bump stop coupled to a proximal side of the apex and separated from the distal tip by a collapsible gap.

5. The catheter of claim 4, wherein the bump stop is configured to contact the distal tip of the shaft to maintain a minimal distance between the apex and the distal tip of the shaft when a force is applied to the expandable distal-end assembly.

6. The catheter of claim 4, wherein the collapsible gap comprises a gap distance of about 3 mm as measured along the longitudinal axis when the expandable distal-end assembly is in an expanded position without force applied to the expandable distal-end assembly.

7. The catheter of claim 1, wherein at least 60 percent of a length at least one spline is non-insulated and is configured to make contact with tissue of the anatomical structure and to deliver ablative energy to the tissue.

8. The catheter of claim 1, wherein the plurality of electrically conductive splines are configured to ablate an area of about 256 mm$^2$ of the tissue.

9. The catheter of claim 1, wherein the non-insulated portion of each spline of the plurality of electrically conductive splines measures between about 10 mm and about 40 mm.

10. The catheter of claim 1,
wherein the shaft is configured to be manipulated to position the plurality of electrically conductive splines within the anatomical structure,
wherein the anatomical structure comprises a heart of a patient,
wherein the non-insulated portions of the plurality of electrically conductive splines are configured to deliver radiofrequency and/or irreversible electroporation pulses to deliver ablative energy to tissue of the heart.

11. An ablation system comprising:
a catheter comprising:
 a shaft,
 a plurality of electrically conductive splines coupled to a distal end of the shaft,
 an apex disposed at a distal end of the catheter, the plurality of electrically conductive splines being coupled to the apex and forming an expandable distal-end assembly between a distal tip of the shaft and the apex, wherein the apex comprises an insulated portion and a non-insulated portion, the non-insulated portion configured to make contact with tissue, and
 one or more electrodes coupled to an insulated portion of one or more splines of the plurality of electrically conductive splines and positioned such that the one or more electrodes are configured to contact the tissue simultaneously with the non-insulated portion of the apex;
a generator; and
a processor configured to:
 control ablation energy provided by the generator to the plurality of electrically conductive splines such that ablation energy is applied to a first spline of the plurality of electrically conductive splines without applying ablation energy to a second spline of the plurality of electrically conductive splines, and
 sense bipolar electrical signals in the tissue between an electrode of the one or more electrodes and the non-insulated portion of the apex.

12. The ablation system of claim 11, wherein each spline of the electrically conductive splines comprises a non-insulated portion, the non-insulated portion being configured to make contact with the tissue of an anatomical structure and electrically ablate the tissue.

13. The ablation system of claim 12, wherein the non-insulated portion of each spline of the plurality of electrically conductive splines measures between about 10 mm and about 40 mm.

14. The ablation system of claim 12,
wherein the shaft is configured to be manipulated to position the plurality of electrically conductive splines within an anatomical structure,
wherein the anatomical structure comprises a heart of a patient,
wherein the non-insulated portions of the plurality of electrically conductive splines are configured to deliver radiofrequency and/or irreversible electroporation pulses to deliver ablative energy to tissue of the heart.

15. The ablation system of claim 11, wherein the catheter comprises a bump stop coupled to a proximal side of the apex and separated from the distal tip by a collapsible gap.

16. The ablation system of claim 15, wherein the bump stop is configured to contact the distal tip of the shaft to maintain a minimal distance between the apex and the distal tip of the shaft when a force is applied to the expandable distal-end assembly.

17. The ablation system of claim 16, wherein the shaft extends along a longitudinal axis and the collapsible gap comprising a gap distance of about 3 mm as measured along the longitudinal axis is provided when the expandable distal-end assembly is in an expanded position without force applied to the expandable distal-end assembly.

18. The ablation system of claim 11, wherein at least 60 percent of a length at least one spline is non-insulated and is configured to make contact with the tissue to deliver ablative energy to the tissue.

19. The ablation system of claim 11, wherein the plurality of electrically conductive splines are configured to ablate an area of about 256 mm$^2$ of the tissue.

20. The ablation system of claim 11, wherein the non-insulated portion of the apex is further configured to deliver ablative energy to the tissue.

* * * * *